United States Patent [19]

Van Doorn et al.

[11] Patent Number: 4,855,399
[45] Date of Patent: Aug. 8, 1989

[54] CARBON MONOXIDE/OLEFIN CO-POLYMERIZATION PROCESS WITH PHOSPHINO SUBSTITUTED SULFONIC ACID CATALYST

[75] Inventors: Johannes A. Van Doorn; Eit Drent; Petrus W. N. M. Van Leeuwen; Nicolaas Meijboom; Aart B. Van Oort; Richard L. Wife, all of Amsterdam, Netherlands

[73] Assignee: Shell Oil Company, Houston, Tex.

[21] Appl. No.: 140,013

[22] Filed: Dec. 31, 1987

[30] Foreign Application Priority Data

Feb. 26, 1987 [NL] Netherlands .................. 8700476

[51] Int. Cl.$^4$ ............................................ C08G 67/02
[52] U.S. Cl. .................................. 528/392; 502/162; 502/168
[58] Field of Search ........................................ 528/392

[56] References Cited

U.S. PATENT DOCUMENTS

| | | | |
|---|---|---|---|
| 2,495,286 | 1/1950 | Brubaker | 260/63 |
| 3,689,460 | 9/1972 | Nozaki | 260/63 |
| 3,694,412 | 9/1972 | Nozaki | 260/63 |

FOREIGN PATENT DOCUMENTS

| | | |
|---|---|---|
| 0121965 | 10/1984 | European Pat. Off. . |
| 0181014 | 5/1986 | European Pat. Off. . |
| 0213671 | 3/1987 | European Pat. Off. . |
| 219906 | 4/1987 | European Pat. Off. . |
| 0222454 | 5/1987 | European Pat. Off. . |
| 248483 | 12/1987 | European Pat. Off. . |
| 1081304 | 3/1965 | United Kingdom . |
| 2058126 | 4/1981 | United Kingdom . |

*Primary Examiner*—Harold D. Anderson
*Attorney, Agent, or Firm*—Dean F. Vance

[57] ABSTRACT

An improved process for the production of linear alternating polymers of carbon monoxide and at least one ethylenically unsaturated hydrocarbon employs a catalyst composition formed from a palladium salt and a phosphino-substituted sulfonic acid.

12 Claims, No Drawings

CARBON MONOXIDE/OLEFIN CO-POLYMERIZATION PROCESS WITH PHOSPHINO SUBSTITUTED SULFONIC ACID CATALYST

FIELD OF THE INVENTION

This invention relates to an improved process for the production of linear alternating copolymers of carbon monoxide and at least one ethylenically unsaturated hydrocarbon. More particularly, the invention relates to the production of such polymers in the presence of a novel catalyst system formed from a palladium compound and a phosphino-substituted sulfonic acid.

BACKGROUND OF THE INVENTION

The class of polymers of carbon monoxide and unsaturated hydrocarbon(s) has been known for a number of years. Brubaker, U.S. Pat. No. 2,495,286, produced such polymers of relatively low carbon monoxide content in the presence of free radical catalysts, e.g., peroxy compounds. U.K. patent No. 1,081,304 illustrates the production of such polymers of higher carbon monoxide content in the presence of alkylphosphine complexes of palladium salts as catalyst. Nozaki extended this process through the use of arylphosphine complexes of palladium salts and certain inert solvents.

More recently, the class of linear alternating polymers of carbon monoxide and at least one ethylenically unsaturated hydrocarbon, also known as polyketones, has become of greater interest because of the greater availability of the polymers. The more recent process for the production of the polyketone polymers is illustrated by a number of published European patent applications including patent application Nos. 0,121,965 and 0,181,014. These publications describe a process employing a catalyst composition formed from a compound of the Group VIII metals palladium, cobalt or nickel, the anion of a non-hydrohalogenic acid having a pKa below 2 and a bidentate ligand of phosphorus, arsenic or antimony. Copending U.S. patent application Ser. No. 088,169, filed Aug. 21, 1987 describes a similar three component catalyst where the earlier bidentate ligand of two phosphorus atoms is replaced by a ligand of defined structure of one phosphorus atom and one nitrogen atom.

The linear alternating polyketone polymers have been shown to be of the general formula —CO+A+ where A is the moiety of ethylenically unsaturated hydrocarbon polymerized through the ethylenic unsaturation. By way of example, when the ethylenically unsaturated hydrocarbon is ethylene, the polymer is represented by the formula —CO+CH$_2$—CH$_2$+. The polymers are relatively high molecular weight thermoplastics having utility in the production of shaped articles including containers for food and drink and parts for the automotive industry. The polymers are characterized by relatively high melting points, generally over 175° C., frequently over 210° C., depending upon the molecular weight and the chemical nature of the polymer.

Although the three-component catalyst system of Group VIII metal compound, anion of non-hydrohalogenic acid and bidentate ligand gives good yields of the polyketone polymer, it would be of advantage in some instances to provide for a less complex catalyst composition.

SUMMARY OF THE INVENTION

The invention relates to the production of linear alternating polymers of carbon monoxide and at least one ethylenically unsaturated hydrocarbon, and to certain novel catalyst compositions useful in the production of such polymers. More particularly, the invention relates to catalyst compositions comprising a palladium compound and a phosphino-substituted sulfonic acid and to the use of the catalyst composition in the production of linear alternating polymers of carbon monoxide and at least one ethylenically unsaturated hydrocarbon.

DESCRIPTION OF THE INVENTION

The palladium compound employed as a catalyst composition component is a palladium salt of an organic acid, preferably an organic monocarboxylic acid of up to 10 carbon atoms. Best results are obtained with a palladium salt of an alkanoic acid such as palladium acetate palladium propionate, palladium isobutyrate, palladium hexanoate and palladium decanoate. Palladium acetate is a particularly preferred catalyst component.

The phosphino-substituted sulfonic acid component of the catalyst composition is an otherwise hydrocarbyl sulfonic acid of up to 30 carbon atoms, preferably up to 20 carbon atoms, having attached to a carbon atom thereof a phosphino substituent whose remaining phosphorus valences are substituted by groups which are hydrocarbyl or substituted hydrocarbyl and are aliphatic or aromatic. Preferred phosphino-substituted sulfonic acids are represented by the formula

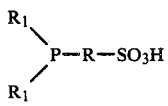

herein $R_1$ independently is an organic group of up to 10 carbon atoms which are hydrocarbyl or substituted hydrocarbyl wherein any non-hydrocarbyl substituents are polar substituents and R is a divalent bridging group of up to 10 carbon atoms having from 1 to 4 carbon atoms inclusive in the bridge between the phosphorus and sulfur atoms.

Illustrative hydrocarbyl $R_1$ groups are alkyl, including aralkyl, such as methyl, ethyl, butyl, benzyl, octyl or decyl, and aryl including alkaryl such as phenyl, naphthyl, tolyl, xylyl and isopropylphenyl. when substituted $R_1$ groups are employed the preferred substituents are alkoxy halo, carboxy, carbalkoxy or dialkylamido. Illustrative of such groups are 2-methoxyphenyl, 2,4-diethoxyphenyl, 2-chlorophenyl, 3-bromophenyl, 2-carboxyphenyl, 4-carbomethoxyphenyl, 2-carbethoxyphenyl and 3-(dimethylamido)phenyl. In general, $R_1$ groups that are the same and are aromatic are preferred over analogous alkyl groups and hydrocarbyl or alkoxy-substituted hydrocarbyl are preferred over other substituents. Phenyl is a particularly preferred $R_1$ group. The divalent hydrocarbyl group R is aliphatic or aromatic and is illustrated by groups such as dimethylene or trimethylene, e.g., —CH$_2$—CH$_2$— or —CH$_2$—CH$_2$—CH$_2$—, or phenylene, particularly o-phenylene.

Thus, illustrative phosphine-substituted sulfonic acids are o-(diphenylphosphino)benzenesulfonic acid, 3-(diphenylphosphino)propanesulfonic acid, 4-[di(2-methoxyphenyl)phosphino]butanesulfonic acid and p-[di(4- ethoxyphenyl)phosphino]benzenesulfonic acid. Use of o-(diphenylphosphino)benzenesulfonic acid as the phosphino-substituted sulfonic acid is particularly preferred.

The phosphino-substituted sulfonic acids are most easily produced by reaction of a phosphino lithium compound and a halo-substituted sulfonic acid or alternatively a phosphino halide and a lithium-substituted sulfonic acid. For example, reaction of diphenylphosphino lithium and 3-chloropropanesulfonic acid affords 3-(diphenylphosphino)propanesulfonic acid and reaction of diphenylchlorophosphine and o-lithium benzenesulfonic acid produces o-(diphenylphosphino)benzenesulfonic acid. Such reactions are broadly conventional and typically take place at low reaction temperatures as in liquid ammonia.

The phosphino-substituted sulfonic acid is employed in a quantity of from about 1 equivalent to about 50 equivalents per gram atom of palladium (as the compound), but preferably in a quantity of from about 1 equivalent to about 25 equivalents per gram atom of palladium.

It is useful on occasion but not required to promote the activity of the catalyst by including within the catalyst composition one or more catalyst modifiers. One such catalyst modifier comprises a salt of a non-noble transition metal and a non-hydrohalogenic acid having a pKa less than about 4, preferably less than about 2. The non-noble transition metals include all the transition metals of Groups IB through VIIB and Group VIII of the Periodic Table of Elements, including the actinides and the lanthanides, but not including the noble metals of Group VIII, i.e., ruthenium, osmium, rhodium, iridium, palladium and platinum, and the noble metals of Group IB, i.e., silver and gold. Examples of non-noble transition metals whose salts are suitably used are the Group IVB metals titanium and zirconium, the Group VB metals vanadium, niobium and tantalum, the Group VIB metals chromium, molybdenum and tungsten, the Group VIIB metal manganese, the Group VIII metals iron, cobalt and nickel, the Group IB metal copper, the Group IIB metal zinc, the lanthanides cerium and lanthanum and the actinides thorium and uranium. Particularly preferred non-noble transition metals are zirconium, vanadium, copper and uranium.

Examples of non-hydrohalogenic acids having a pKa less than about 4 (measured in aqueous solution at 18° C.), the non-noble transition metal salts of which are useful catalyst modifiers, are inorganic acids such as sulfuric acid, and organic acids including the sulfonic acids such as p-toluenesulfonic acid and the carboxylic acids trifluoroacetic acid. Acids having a pKa less than about 2 are generally preferred and particularly good results are obtained through the use of non-noble transition metal salts of sulfuric acid or p-toluenesulfonic acid. If such a salt is included as a catalyst modifier, it is preferably employed in a quantity of up to abut 200 equivalents per gram atom of palladium, more preferably from about 1 equivalent to about 100 equivalent per gram atom of palladium.

A second type of catalyst modifier to optionally be employed comprises a quinone, preferably a quinone of up to 15 carbon atoms. Illustrative quinones are benzoquinones, naphthaquinones and anthraquinones but preferred quinones are benzoquinones, particularly 1,4-benzoquinone. When quinone is employed, quantities of quinone up to about 10,000 mol per gram atom of palladium are useful, particularly quantities from about 10 mol to about 5,000 mol per gram atom of palladium.

Suitable ethylenically unsaturated hydrocarbons useful as precursors of the polyketone polymers have from 2 to 20 carbon atoms inclusive, preferably up to 10 carbon atoms, and are aliphatic such as ethylene and other α-olefins including propylene, 1-butene, 1-octene and 1-decene, or are arylaliphatic containing an aryl substituent on an otherwise aliphatic molecule, particularly an aromatic substituent on a carbon atom of the ethylenic unsaturation. Illustrative of this latter class of ethylenically unsaturated hydrocarbons are styrene, p-methylstyrene, p-ethylstyrene and m-methylstyrene. Preferred polyketone polymers are copolymers of carbon monoxide and ethylene or are terpolymers of carbon monoxide, ethylene and a second hydrocarbon of at least 3 carbon atoms, particularly an α-olefin such as propylene.

The structure of the preferred polymers is that of a linear alternating polymer of carbon monoxide and unsaturated hydrocarbon and the polymer will have substantially one molecule of carbon monoxide for each molecule of hydrocarbon. When terpolymers of carbon monoxide, ethylene and a second hydrocarbon, i.e., a hydrocarbon of at least 3 carbon atoms, is produced, there will be at least two units incorporating a moiety of ethylene for each moiety incorporating a moiety of the second hydrocarbon, preferably from about 10 to about 100 units incorporating a moiety of ethylene per unit incorporating a moiety of second hydrocarbon. The polymer chain is therefore represented by the formula

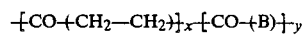

where B is the moiety obtained by the polymerization of the second ethylenically unsaturated hydrocarbon through the ethylenic unsaturation. The —CO—(CH$_2$—CH$_2$)— units and the —CO—(B)— units are found randomly throughout the polymer chain and the ratio of y:x is no more than about 0.5. In the modification of the invention wherein copolymers of carbon monoxide and ethylene are produced without the presence of a second hydrocarbon, the polymers are represented by the above formula wherein y=0. When y is other than 0, i.e., terpolymers are produced, ratios of y:x from about 0.01 to about 0.1 are preferred. The end groups or "caps" of the polymer chain will depend upon what materials are present during the production of the polymer and whether and how the polymer has been purified. The precise nature of the end groups is of little significance with regard to the overall properties of the polymer so that the polymer is fairly represented in terms of the polymer chain as depicted above.

Of particular interest are those polymers of molecular weight from about 1,000 to about 200,000, particularly those of molecular weight from about 10,000 to about 50,000 containing substantially equimolar quantities of carbon monoxide and unsaturated hydrocarbon. The physical properties of such polymers will depend in part on the molecular weight of the polymer, whether the polymer is a copolymer or a terpolymer and the relative proportion of any second hydrocarbon present. Typical melting points of such polymers are from about 175° C. to about 300° C., more frequently from about 210° C. to about 270° C.

The reactants and catalyst composition components are contacted in a reactor such as an autoclave where conditions of elevated temperature and pressure can be maintained. The mechanical nature of the reactor is not critical but best results are obtained if reactant-catalyst contact is promoted as by shaking or stirring. The quantity of catalyst to be employed will be a catalytic quantity. Amounts of catalyst are sufficient to provide from about $1 \times 10^{-7}$ gram atom to about $1 \times 10^{-3}$ gram atom of palladium per mol of unsaturated hydrocarbon to be polymerized, preferably amounts sufficient to provide from abut $1 \times 10^{-6}$ gram atom to about $1 \times 10^{-4}$ gram atom of palladium per mol of unsaturated hydrocarbon. The molar ratio of ethylenically unsaturated hydrocarbon to carbon monoxide to be utilized in the process of the invention will be from about 10:1 to about 1:5 but preferably will be from about 5:1 to about 1:2.

Polymerization is conducted under polymerization conditions in the gaseous phase but preferably in a liquid phase in the presence of an inert diluent such as a lower alkanol, e.g., methanol or ethanol. Suitable reaction temperatures are from about 20° C. to about 200° C. with preferred temperatures being from about 30° C. to about 150° C. Typical reaction pressures are from about 1 bar to about 200 bar, preferably from about 20 bar to about 100 bar. Subsequent to reaction, the polymer product is recovered by conventional methods such as filtration or decantation. The polymer will on occasion contain residues of catalyst which are removed, if desired, by contact with a solvent which is selective for the residues.

The polymers are compounded when desired with conventional additives such as stabilizers, antioxidants, fillers and reinforcements or are blended with other polymeric materials to produce compositions of modified properties.

The polyketones are in general premium thermoplastics of established utility. Such applications include the production of containers for food and drink as by thermoforming of polyketone sheet, the production of shaped parts for the automotive industry produced as by injection molding and the production of wires and cables produced by extrusion.

The invention is further illustrated by the following Comparative Example (not of the invention) and Illustrative Embodiments which should not be regarded as limiting. All carbon monoxide/ethylene copolymers produced had a melting point of 257° C. and were shown by $^{13}$C-NMR to consist of units of the formula —CO—(C$_2$H$_4$)—. The carbon monoxide/ethylene/propylene terpolymer had a melting point of 220° C. and was shown by $^{13}$C-NMR to consist of units of the formulas —CO—(C$_2$H$_4$)— and —CO—(C$_3$H$_6$)—distributed randomly throughout the terpolymer.

ILLUSTRATIVE EMBODIMENT I

The compound o-(diphenylphosphino)benzenesulfonic acid was produced by adding 62.5 ml of a 1.6 molar solution of butyl lithium in hexane to a mixture of 16.4 g of lithium benzenesulfonate and 250 ml of dry tetrahydrofuran in a mechanically stirred reaction vessel kept at −78° C. by cooling. After 2 hours, 18.25 ml of diphenylchlorophosphine was added to the reaction mixture. the cooling was stopped and the resulting reaction mixture was stirred for 12 hours. To the mixture were added 100 ml of water and 150 ml of dimethyl ether. The aqueous layer was separated and evaporated to dryness. The dry residue was then dissolved in 300 ml of water and acidified with 6N hydrochloric acid. The o-(diphenylphosphino)benzenesulfonic acid was removed by filtration, washed with water and dried.

ILLUSTRATIVE EMBODIMENT II

The compound 3-(diphenylphosphino)propanesulfonic acid was produced by the following procedure. To a solution of 3.8 g of sodium in 500 ml of liquid ammonia in a stirred reaction vessel maintained at −78° C. by cooling, 21.8 g of triphenylphosphine was added. After 30 minutes, 4.3 g of ammonium chloride was added and after an additional 30 minutes, 15 g of sodium 3-chloropropanesulfonate was added. The cooling was stopped and 400 ml of tetrahydrofuran was added to the reaction mixture. After the ammonia was evaporated, the mixture was refluxed for some time and then evaporated. The residue thereby obtained was washed with hot ethanol and the product was dried in vacuo to yield a mixture of sodium 3-(diphenylphosphino)propanesulfonate and sodium chloride. The mixture was treated with aqueous trifluoroacetic acid to afford the 3-(diphenylphosphino)propanesulfonic acid.

COMPARATIVE EXAMPLE

A carbon monoxide/ethylene copolymer was produced by charging to a mechanically stirred autoclave of 250 ml capacity a catalyst solution comprising 50 ml of methanol, 0.1 mmol of palladium acetate, 2.0 mmol of p-toluenesulfonic acid and 0.3 mmol of triphenylphosphine. The air present in the autoclave was removed by evacuation and ethylene was added until a pressure of 30 bar was reached and carbon monoxide was added until a pressure of 60 bar was reached. After maintaining the reactor contents at 110° C. for 5 hours, polymerization was terminated by cooling to room temperature and releasing the pressure. The polymer product was removed by filtration, washed with methanol and dried in vacuo. From the weight of polymer obtained, the calculated polymerization rate was 5 g of copolymer/g palladium/hr.

ILLUSTRATIVE EMBODIMENT III

A copolymer of carbon monoxide and ethylene was produced by the procedure of the Comparative Example except that the catalyst solution contained 0.15 mmol of o-(diphenylphosphino)benzenesulfonic acid instead of the p-toluenesulfonic acid and the triphenylphosphine, the ethylene added was added to give a pressure of 20 bar and carbon monoxide was added to give a pressure of 40 bar, and the reaction temperature was 80° C. instead of 110° C. The calculated rate of polymerization was 90 g of copolymer/g palladium/hr.

ILLUSTRATIVE EMBODIMENT IV

A series of copolymers of carbon monoxide and ethylene were prepared by the procedure of Illustrative Embodiment III except that the catalyst solution contained 0.5 mmol of a non-Group VIII transition metal salt. in each case the rate of polymerization was calculated. The results are shown in Table I.

TABLE 1

| Metal Salt | Rate of Polymerization, g Copolymer/g Pd/hr |
|---|---|
| Copper p-toluenesulfonate | 115 |
| Vanadyl sulfate | 96 |
| Zirconium sulfate | 110 |
| Uranyl sulfate | 120 |

ILLUSTRATIVE EMBODIMENT V

A polymer of carbon monoxide, ethylene and propylene was produced by substantially the same procedure as that of the Comparative Example except that a) the catalyst solution contained 0.15 mmol of o(diphenylphosphino)benzenesulfonic acid instead of the p-toluenesulfonic acid and triphenylphosphine, and additionally contained 0.5 mmol of copper p-toluenesulfonate, b) the autoclave additionally contained 30 ml of liquid propylene, c) ethylene was introduced until a pressure of 25 bar was reached and carbon monoxide was added until a pressure of 55 bar was reached, and d) the reaction temperature was 80° C. instead of 110° C.

The calculated polymerization rate was 175 g of terpolymer/g palladium/hr.

ILLUSTRATIVE EMBODIMENT VI

A copolymer of carbon monoxide and ethylene was produced by the general procedure of the Comparative Example except that the catalyst solution comprised 100 ml of methanol, 0.1 mmol of palladium acetate and 0.1 mmol of o-(diphenylphosphino)benzenesulfonic acid, the reaction temperature was 120° C. instead of 110° C. and the reaction time was 1.5 hr instead of 5 hours.

The calculated polymerization rate was 900 g of copolymer/g palladium/hr.

ILLUSTRATIVE EMBODIMENT VII

A copolymer of ethylene and carbon monoxide was produced by the general procedure of the Comparative Example except that a) the autoclave had a capacity of 100 ml instead of 250 ml, b) the catalyst solution comprised 20 ml of methanol, 0.12 mmol of palladium acetate and 0.24 mmol of 3-(diphenylphosphino)propanesulfonic acid, c) ethylene was added until a pressure of 15 bar was reached and carbon monoxide was added until a pressure of 30 bar was reached, and d) the reaction temperature was 120° C. instead of 110° C. and the reaction time was 40 minutes instead of 5 hours.

The calculated polymerization rate was 80 g of copolymer/g palladium/hr.

What is claimed is:

1. The process of producing a linear alternating polymer of carbon monoxide and at least one ethylenically unsaturated hydrocarbon by contacting under polymerization conditions the carbon monoxide and hydrocarbon in the presence of a catalyst composition formed from a palladium compound and a phosphino-substituted sulfonic acid of up to 30 carbon atoms.

2. The process of claim 1 wherein the sulfonic acid is represented by the formula

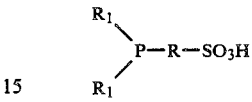

wherein $R_1$ independently is an organic group of up to 10 carbon atoms selected from hydrocarbyl groups or substituted hydrocarbyl groups wherein any substituents are polar substituents and R is a divalent hydrocarbyl bridging group of up to 10 carbon atoms and from 1 to 4 carbon atoms inclusive in the bridge between the phosphorus and sulfur atoms.

3. The process of claim 2 wherein the palladium compound is a palladium carboxylate.

4. The process of claim 3 wherein the polymer has recurring units of the structure

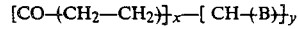

wherein B is the moiety of an ethylenically unsaturated hydrocarbon of at least 3 carbon atoms polymerized through the ethylenic unsaturation and the ratio of y:x is no more than about 0.5.

5. The process of claim 4 wherein y is zero.

6. The process of claim 5 wherein $R_1$ is phenyl and R is o-phenylene.

7. The process of claim 5 wherein $R_1$ is phenyl or alkoxyphenyl and R is trimethylene.

8. The process of claim 7 wherein $R_1$ is phenyl.

9. The process of claim 4 wherein the ratio of y:x is from about 0.01 to abut 0.1 and B is a moiety of propylene.

10. The process of claim 9 wherein $R_1$ is phenyl and R is o-phenylene.

11. The process of claim 9 wherein $R_1$ is phenyl or alkoxyphenyl and R is trimethylene.

12. The process of claim 11 wherein $R_1$ is phenyl.